(12) United States Patent
Matsui et al.

(10) Patent No.: US 6,939,699 B2
(45) Date of Patent: Sep. 6, 2005

(54) DNA HELICASE

(75) Inventors: Ikuo Matsui, Tsukuba (JP); Hiroki Higashibata, Tsukuba (JP); Yutaka Kawarabayashi, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/373,090

(22) Filed: Feb. 26, 2003

(65) Prior Publication Data

US 2003/0232357 A1 Dec. 18, 2003

(30) Foreign Application Priority Data

Mar. 1, 2002 (JP) ........................................ 2002-055991

(51) Int. Cl.[7] ............... C12N 9/10; C12N 9/14

(52) U.S. Cl. ................ 435/193; 435/194; 435/183; 435/195; 530/350

(58) Field of Search .............................. 435/183, 193; 530/350, 23.1, 23.3

(56) References Cited

PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Kawarabayasi et al., Database PIR 78, Accession No. C71231, Aug. 1998.*
EP Search Report dated Sep. 1, 2003 for Ref. 303025EP/JND/AV, App. No. 03251213.9–1521–.
Database EM_PRO Online! EMBL; Jun. 17, 1998 Director–General of Giotechnology Center et al.: "Pyrococcus horikoshi OT3 genomic DNA, 1–287000 nt. Position 1/7" retried from EBI Database accession no. AP000001 XP002251724 *abstract*.
Database Swall Online! Aug. 1, 1998 Kawarabayasi et al.: Hypothetical protein PH0109 retried from EBI Database accession No. 057849 XP002251725 *the whole document*.
Kawarabayasi et al.: "Complete sequence and gene organization of the genome of a hyperthermophilic Archaebacterium, Pyrococcus horikoshii OT3" DNA Research, vol. 5, 1998, p.p. 55–76, XP002948248 "p.p. 55–56, left–hand column, paragraph 2* *p. 74, line 11".
Kyrpides et al.: "Transcription in Archaea" Prodeedings of the National Academy of Sciences, vol. 96, Jul. 1999, p.p. 8545–8550, XP002251723 "table 3".
Database Swall Online! May 1, 2000 Heilig, R.: "DNA helicase related protein" retrieved from EBI Database accession No. Q9V2G5 XP002251726 *the whole document*.
Database GSP Online! EMBL; May 14, 2001 Hogrefe et al.: "Recombinant P. furiosus helicase 7" retrieved from EBI Database accession No. AAB62030 XP002251727 & WO 01 09347 A (Stratagene) Feb. 8, 2001 *the whole document*.

* cited by examiner

Primary Examiner—Richard Hutson
(74) Attorney, Agent, or Firm—Sughrue Mion, PLLC

(57) ABSTRACT

The present invention provides a heat-stable enzyme having a DNA helicase activity, and preferably a structure-specific endonuclease activity. This enzyme can be obtained by cloning a gene encoding the enzyme from chromosomal DNA of a hyperthermophile, preferably a sulfur-metabolizing thermophilic archaebacteria, incorporating the gene into an expression vector, introducing the vector into a host such as *Escherichia coli* in the usual manner to create a transformant, and culturing the transformant.

2 Claims, 8 Drawing Sheets

Preparation of two kinds of labeled DNA substrates for determination of unwinding direction
Symbol ✱ indicates labeled terminus

FIG. 2

Endonuclease activity measuring substrate

Substrate (c)  Substrate (d)  Substrate (e)  Substrate (f)

5'*-$T_{40}$-$dX_{80}$   5'*-$U_{12}$-$T_{28}$-$dX_{30}$   5'*   5'*

SDS-PAGE of purified Dna2

FIG. 4

Sequence motif conserved in both Dna2 and Dna2Pho
Numerals indicate residue No. from protein terminus and the number of residues between motifs

|  |  | I |  | Ia |  | II |  | III |  |
|---|---|---|---|---|---|---|---|---|---|
| S. cerevisiae Dna2 | 1071 | ILGMPGTGKT | TVIA 13 | LLTSYTHSAV | DNILIKL 66 | YVILDEASQI | S 13 | FIMVGDHYQL | PP 25 |
| S. pombe Dna2 | 951 | ILGMPGTGKT | TTIS 13 | LLTSFTHLAV | DNILIKI 65 | YCIIDEASQI | P 13 | FVLVGDHYQL | PP 25 |
| P. horikoshi PH0109 | 738 | LQGPPGTGKT | SGAI 20 | IVIALSHRAV | NEALIRT 77 | LVVIDEASML | D 14 | VLLVGDHRQM | QP 154 |

|  | IV |  | V |  | VI |  |
|---|---|---|---|---|---|---|
| S. cerevisiae Dna 2 | ESVAELTLQY | RMCGDI 129 | DKKCIIISM 17 | RVNVAMTRAK | S 88 |
| S. pombe Dna2 | EAVTTERLQY | RMNEDI 125 | DKDIILISF 17 | RLNVALSRAK | V 88 |
| P. horikoshi PH0109 | GIDVGVVPY | RAQKRL 8 | VDIVERFQG | EKDVIIVSM 19 | RLNVAGSRAK | E 58 |

| S. cerevisiae Dna 2 | |
|---|---|
| Motif Number | SEQ ID NO: |
| I | 5 |
| Ia | 6 |
| II | 7 |
| III | 8 |
| IV | 9 |
| V | 10 |
| VI | 11 |

| S. pombe Dna2 | |
|---|---|
| Motif Number | SEQ ID NO: |
| I | 12 |
| Ia | 13 |
| II | 14 |
| III | 15 |
| IV | 16 |
| V | 17 |
| VI | 18 |

| P. horikoshi PH0109 | |
|---|---|
| Motif Number | SEQ ID NO: |
| I | 19 |
| Ia | 20 |
| II | 21 |
| III | 22 |
| IV | 23 |
| V | 24 |
| VI | 25 |

Structure-specific endonuclease activity
M indicates molecular weight marker (2mer - 63mer)

DNA HELICASE

FIELD OF THE INVENTION

The present invention relates to a heat-stable enzyme having a 5'-3' DNA helicase activity, a DNA molecule encoding the enzyme, an expression vector including the DNA molecule, a method of producing a transformant by the expression vector, and a method of producing the heat-stable enzyme using the transformant.

BACKGROUND OF THE INVENTION

The yeast protein Dna2, originated from the budding yeast (Saccharomyces cerevisiae), is well known as an enzyme having a 5'-3' DNA helicase activity and a structure-specific endonuclease activity. The properties of Dna2 have been recently reported in detail (S. Bae, K. Bae, J. Kim, and Y. Seo, "RPA governs endonuclease switching during processing of Okazaki fragments in eukaryotes" (2001) Nature, 412, 456–461).

Dna2 is an essential enzyme in DNA replication and repair, and specifically plays a roll in unwinding a double helix into separate single strands during DNA replication initiation, maturating Okazaki fragments during lagging strand replication, and repairing double-strand breaks. While various DNA helicases including Dna2 have been found in viruses, bacteria and eukaryotes, most of them are originated from mesophiles. Thus, such DNA helicases are rapidly deactivated under conditions causing heat-denaturation of double-stranded DNA.

If a heat-stable enzyme having a 5'-3' DNA helicase activity is discovered, all processes involving heat-denaturation of double-stranded DNA at 94° C. or greater, rapid cooling of the heat-denatured double-stranded DNA and an enzymatic reaction could be carried out in one tube. Such a heat-stable enzyme would open the way for establishing a combinational experimental system of a DNA replication-repair conjugation system and a DNA amplification reaction (PCR) or the like, and in the development of new in vitro gene replication or mutation methods. Thus, there is a strong need for an enzyme capable of unwinding a double helix into separate single strands during DNA replication initiation, maturating Okazaki fragments during lagging strand replication, and repairing double-strand breaks, even under stringent conditions.

SUMMARY OF THE INVENTION

It is therefore an object of the present invention to provide an enzyme having heat stability and a DNA helicase activity, and preferably, a structure-specific endonuclease activity as well.

In view of the above goal, the inventors focused on hyperthermophilic archaebacteria growing at 90 to 100° C., and identified a gene having the potential of encoding a protein that exhibits the enzymatic activities in question. The inventors then produced an enzyme from the gene by using *Escherichia coli*, and verified that the produced enzyme could maintain an acceptable stability at a high temperature (75° C. or more) and exhibit DNA helicase/structure-specific endonuclease activities. Based on this knowledge, the inventors have finally accomplished the present invention.

According to a first aspect of the present invention, there is provided a DNA encoding a protein, wherein said protein comprises an amino acid sequence shown in SEQ ID NO:1, or an amino acid sequence having one or more amino acid deletions, substitutions or insertions relative to the amino acid sequence shown in SEQ ID NO:1.

According to a second aspect of the present invention, there is provided a DNA comprising a nucleotide sequence shown in SEQ ID NO:2, or a nucleotide sequence having one or more nucleotide deletions, substitutions or insertions relative to the nucleotide sequence shown in SEQ ID NO:2.

According to a third aspect of the present invention, there is provided a DNA comprising a nucleotide sequence shown in SEQ ID NO:2 which has ATG substituted for the initiation codon thereof.

According to a fourth aspect of the present invention, there is provided a DNA which is hybridizable to the DNA set forth in any of the first to third aspects of the present invention, under a stringent condition.

Preferably, in the DNA set forth in any of the first to fourth aspects of the present invention, the DNA encodes a protein having a 5'-3' DNA helicase activity. More preferably, the above protein additionally has a structure-specific endonuclease activity.

According to a fifth aspect of the present invention, there is provided an expression vector containing the DNA set forth in any of the first to fourth aspects of the present invention.

According to a sixth aspect of the present invention, there is provided a transformant which is transformed by the expression vector set forth in the fifth aspect of the present invention.

According to a seventh aspect of the present invention, there is provided a method for producing a DNA helicase, wherein the transformant set forth in the sixth aspect of the present invention is cultured under the condition such that the protein encoded by the DNA set forth in any of the first to fourth aspects of the present invention is expressed.

According to an eighth aspect of the present invention, there is provided a protein comprising an amino acid sequence shown in SEQ ID NO:1, or an amino acid sequence having one or more amino acid deletions, substitutions or insertions relative to the amino acid sequence shown in SEQ ID NO:1. Preferably, the protein has a 5'-3' DNA helicase activity. More preferably, the protein additionally has a structure-specific endonuclease activity.

The protein may be produced through the method set forth in the seventh aspect of the present invention.

According to a ninth aspect of the present invention, there is provided an enzyme having heat stability and a 5'-3' DNA helicase activity. Preferably, the enzyme additionally has a structure-specific endonuclease activity.

BRIEF DESCRIPTION OF THE DRAWINGS

FIG. 2 is a schematic diagram showing respective structures of substrates used for determining an endonuclease activity in the enzymatic protein of the invention.

FIG. 4 is a diagram showing a sequence motif conserved in both the yeast Dna2 protein and the Dna2Pho of the present invention.

DETAILED DESCRIPTION OF THE INVENTION

The present invention will now be described in detail.

In the present invention, a heat-stable enzyme having a 5'-3' DNA helicase activity is produced by cloning a gene encoding an enzyme which is obtained from chromosomal DNA of a hyperthermophile, preferably a sulfur-metabolizing thermophilic archaebacterium, incorporating the cloned gene into an expression vector, introducing the expression vector into a host such as *Escherichia coli* in the usual manner, to obtain a transformant, and culturing the transformant.

The gene encoding the heat-stable enzymatic protein having the 5'-3' DNA helicase activity according to the present invention, and the enzymatic protein were prepared through the following process.

Chromosomal DNA of *Pyrococcus horikoshi* (deposited Mar. 15, 2002 with the Institute of Physical & Chemical Research, Japan Collection of Microorganism (JCM) as deposit number 9974, and transferred and accepted by the International Depositary Authority under the terms of the Budapest Treaty at the National Institute of Advanced Industrial Science and Technology (AIST), Tsukuba Central 6, 1-1, Higashi 1-Chome Tsukuba-shi, Ibaraki-ken 305-8566 Japan, on Feb. 17, 2003), a sulfur-metabolizing thermophilic archaebacteria, was digested by the restriction enzyme HindIII, and the obtained DNA fragments were ligated into the vectors pBAC198L and pFOS 1. The vectors were then introduced into *Escherichia coli*. Then, the obtained *Escherichia coli* populations, also having antibiotic chloramphenicol resistance, were used as BAC and Fosmid libraries. Then, clones encompassing the entire length of the chromosome of the strain JCM9974 were selected from the libraries, and each of the clones was aligned. By the DNA sequencing of each clone, a gene (PHO109) having a motif of a known DNA helicase was identified by homology searching with a computer.

Then, the putative 5'-non-coding region of PHO109 was fully examined, since the initiation codon of hyperthermophilic archaebacterium can be not only ATG but also TTG. Consequently, an extended ORF encoding Dna2Pho, with TTG as the initiation codon, was identified. The extended ORF includes nucleotide sequence encoding an additional 122 amino acid residues on the N-terminal side, in comparison to PHO109.

Figure 8:
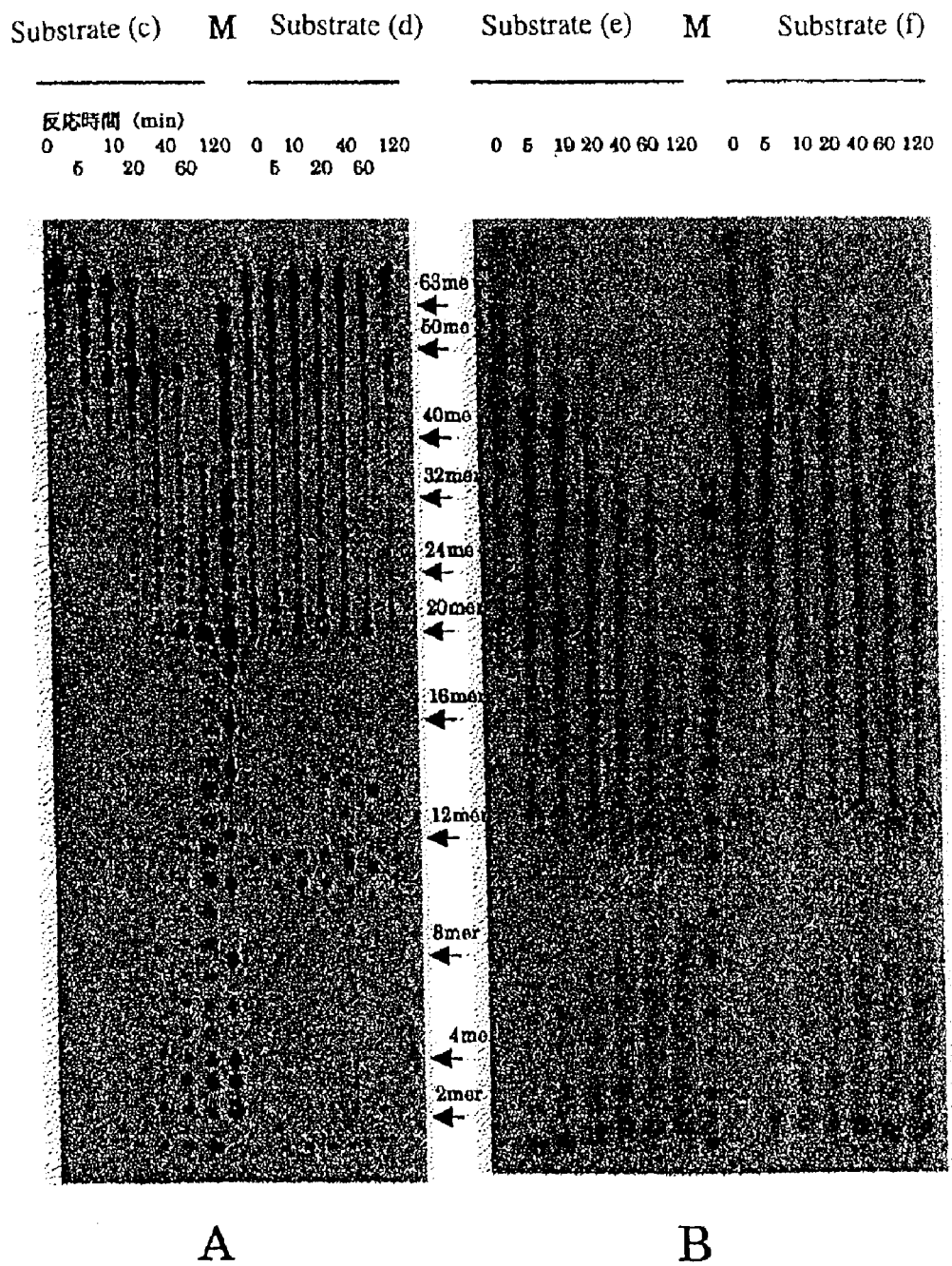
FIG. 8 is an autoradiographic picture of electrophoresis patterns of enzymatic reaction products, which shows that the enzymatic protein of the present invention has an endo-nuclease activity specific for its substrate structure.

Next, *Escherichia coli* cells were transformed with an expression vector containing the Dna2Pho gene. The recombinant Dna2Pho protein expressed by the cells was then isolated from the transformed cells and purified. The purified protein had a molecular weight of about 152,000 Daltons and exhibited a 5'-3' DNA helicase activity. In addition, it was confirmed that the obtained protein exhibited an endonuclease activity when the concentration of $Mg^{2+}$ ions was increased up to a given value, and the endonuclease activity was structure-specific as seen in FIG. 8-A, B.

The enzyme exhibited excellent heat stability, specifically a half-life period of 30 minutes or more at 75° C. in 50 mM Tris-HCl buffer solution (pH 7.5).

This enzyme will be occasionally abbreviated as "Dna2Pho" hereinafter.

The amino acid sequence of the above heat-stable enzymatic protein having the 5'-3' DNA helicase activity and the base sequence of the gene encoding this protein are fundamentally shown in SEQ ID NOS:1 and 2, respectively. However, as long as the enzymatic protein to be obtained has the 5'-3' DNA helicase activity, the base sequence of a gene to be used may be changed to modify a part of the amino acid sequence of the enzymatic protein, or a part of the base sequence of the gene may be changed depending on hosts or the like to facilitate the expression of the desired enzymatic protein.

A method of producing an enzymatic protein according to the invention will be described below.

The gene obtained in the above way for encoding the enzymatic protein (Dna2Pho) having the 5'-3' DNA helicase activity is ligated into an expression vector by using a ligase such as T4 ligase. When *Escherichia coli* are used as a host, pET21b may be used as the expression vector to obtain a fusion protein having a histidine tag on the C-terminus thereof.

Then, the expression vector containing the gene encoding the enzymatic protein (Dna2Pho) having the 5'-3' DNA helicase activity is introduced into the host to obtain a transformant. For example, *Escherichia coli* BL21 (DE3) Codon Plus RIL may be used as the host.

The obtained transformant is cultured in the usual manner, and the cultured solution is centrifuged to collect cells. The collected cells are suspended in buffer solution, and then disrupted. Then, the supernatant is subjected to an affinity chromatography or the like to isolate and purify the enzymatic protein of the present invention.

A particularly noteworthy point of the present invention is that the gene encoding the enzymatic protein (Dna2Pho) having the 5'-3' DNA helicase activity was identified and cloned from sulfur-metabolizing thermophilic archaebacteria for the first time ever. Since the gene of the enzymatic protein (Dna2) having the 5'-3' helicase activity in yeast and the corresponding gene of the sulfur-metabolizing thermophilic archaebacteria have very few homologous regions therebetween, it has heretofore been difficult to identify and clone a gene of an enzymatic protein having a 5'-3' DNA helicase activity from a sulfur-metabolizing thermophilic archaebacteria by using the base sequence of the Dna2 gene as a marker. In the present invention, a 5'-3' DNA helicase gene is identified and cloned from *Pyrococcus horikoshi*, and its nucleotide sequence is determined. Thus, the nucleotide sequence can be used, for example, to produce a probe which allows a gene of a heat-stable 5'-3' DNA helicase to be readily obtained from other sulfur-metabolizing thermophilic archaebacteria or hyperthermophiles. In addition, the method of the present invention can be used to produce the heat-stable 5'-3' DNA helicase (Dna2Pho).

While various Examples of the present invention will be described below, the present invention is not limited thereto.

EXAMPLE 1

Culture of Bacteria

*Pyrococcus horikoshi* (Deposition No: JCM9974) obtained from the JCM (The Institute of Physical and Chemical Research, Japan Collection of Microorganisms) was cultured as follows.

13.5 g of sodium chloride, 4 g of $Na_2SO_4$, 0.7 g of KCl, 0.2 g of $NaHCO_3$, 0.1 g of KBr, 30 mg of $H_3BO_3$, 10 g of $MgCl_2.6H_2O$, 1.5 g of $CaCl_2$, 25 mg of $SrCl_2$, 1.0 ml of resazurin solution (0.2 g/L), 1.0 g of yeast extract, and 5 g of bactopeptone were dissolved in 1 L of water. The obtained solution was adjusted to pH 6.8, and sterilized under pressure. Then, dry-heat sterilized elemental sulfur was added to the sterilized solution at 0.2%. This medium was saturated with argon to give an anaerobic environment, and the strain JCM9974 was inoculated thereinto. The presence of an anaerobic environment in the medium was confirmed by adding an $Na_2S$ solution into the culture solution and checking that the pink resazurin solution was not stained. This culture solution was incubated at 95° C. for 2 to 4 days, and then cells were collected through centrifugation.

EXAMPLE 2

Preparation of Chromosomal DNA

Chromosomal DNA of *Pyrococcus horikoshi* JCM9974 was prepared through the following process. After completion of the culture, the cultivated cells were collected through centrifugation at 5000 rpm for 10 minutes. The collected cells were rinsed twice with 10 mM Tris (pH 7.5), 1 mM EDTA solution, and then enclosed in an InCert Agarose (made by FMC Co., Ltd.) block. The chromosomal DNA was separated and prepared in the Agarose block by treating the block with 1% N-lauroylsarcosine, 1 mg/ml protease K solution.

EXAMPLE 3

Preparation of Library Clones Containing Chromosomal DNA

The chromosomal DNA obtained in Example 2 was partially digested with restriction enzyme HindIII, and then fragments each having a length of about 40 kb were prepared through agarose gel electrophoresis. With T4 ligase, the DNA fragments were ligated into respective Bac vectors pBAC108L and pFOS1 which had been completely digested by restriction enzyme HindIII. When the former vector was used, the JCM9974 DNA-containing pBAC108L vector was introduced into *Escherichia coli* through electroporation immediately after completion of the ligation. When the latter vector pFOS 1 was used, the JCM9974 DNA-containing vector was packed into a λ phage particle *in vitro* by use of GIGA Pack Gold (made by Stratagene) after completion of the ligation, and then used to infect *Escherichia coli*. As both vectors also contained a chloramphenicol-resistance gene, transformed populations of *Escherichia coli* having chloramphenicol resistance were used as BAC and Fosmic libraries. Clones suitable for covering the chromosome of JCM9974 were selected from the libraries, and then aligned in chromosomal order.

EXAMPLE 4

Determination of Base Sequence of BAC or Fosmid Clone

The base sequence of the aligned BAC or Fosmid clone was determined through the following process. The selected BAC and Fosmid clone DNAs were collected from the *Escherichia coli* transformants and fragmented through ultrasonication. The resulting DNA fragments, each having a length of 1 kb and 2 kb, were collected through agarose gel electrophoresis. These fragments were inserted into the HincII restriction enzyme site of the plasmid vector pUC 118 to prepare 500 shotgun clones for each of the BAC and Fosmid clones. The respective base sequences of the shotgun clones were determined by use of an Automatic Base-Sequence Reader 373 or 377 made by Perkin-Elmer/ABI. The base sequences obtained from the shotgun clones were aligned and editing by use of base-sequence automatic alignment software (Sequencher) to determine the entire base sequence of each of BAC and Fosmid clone.

EXAMPLE 5

Identification of Dna2Pho Gene

The determined sequences of the BAC and Fosmid clones were analyzed using a large scale computer to identify a gene (PHO109) encoding a function-unknown protein containing a DNA helicase motif. The putative 5'-non-coding region of the ORF was fully examined, since the initiation codon of hyperthermophilic archaebacterium can be not only ATG but also TTG. Consequently, an extended ORF encoding Dna2Pho was identified that included nucleotide sequence encoding an additional 122 amino acid residues on the N-terminal side, in comparison with PHO109. The elongated ORF encoding Dna2Pho with TTG as its initiation codon is shown in SEQ ID NO:2.

EXAMPLE 6

Construction of Expression Plasmid

In order to introduce restriction enzyme sites (NdeI and SalI) at both ends of the ORF region of the Dna2Pho gene by PCR, DNA primers were synthesized. Further, the upper primer was constructed so as to change the initiation codon from TTG to ATG.

Upper Primer,

5'- GTAGAGGTGGAAAC<u>ATATG</u>GAATTTGGG-GAGTTA CATCCCAGCG-3' (SEQ ID NO:3) (wherein the underlined part represents the NdeI site).

Lower Primer,

5'- CTCGAGTGCGGCCGCAAGCTT<u>GTCGAC</u>CTCTCC-AGCCCACCTAAACAC-3' (SEQ ID NO:4) (wherein the underlined part represents the SalI site)

After the PCR reaction, the isolated gene fragment was completely digested by the restriction enzymes (NdeI and SalI) (at 37° C. for 2 hours), and then the digested fragment was purified.

pET21b (made by Novagen) was cleaved by restriction enzymes NdeI and XhoI, and purified. The obtained fragments were ligated with the above gene fragments encoding Dna2Pho at 16° C. for 2 hours using T4 ligase. A portion of the ligated DNA was introduced into competent *E. coli* strain XL1-BlueMRF' to obtain a transformant colony. The obtained colony was purified through an alkali method to obtain an expression plasmid (pET21b/Dna2Pho). When this expression plasmid is used, Dna2Pho will be produced as a fusion protein having a histidine tag added to its C-terminus.

EXAMPLE 7

Expression of Recombination Gene

Competent cells of *Escherichia coli* (*E. coli* BL21 (DE3) CodonPlus RIL made by Novagen) were thawed, and 0.1 ml of the thawed cells was transferred to each of two Falcon tubes. Then, each of the Falcon tubes was supplemented with 0.005 ml of the pET21b/Dna2Pho expression plasmid solution. The respective mixtures were left on ice for 30 minutes, and then heat-shocked at 42° C. for 30 seconds. Each of the Falcon tubes was further supplemented with 0.9 ml of SOC medium, and the cells in the Falcon tubes were shaking-cultured at 37° for 1 hour. Then, the cells were placed on a 2YT agar plates containing ampicillin, and cultured at 37° C. for one night to obtain a transformant Escherichia coli BL21(DE3) CodonPlus RIL/pET21b /Dna2Pho.

A single colony of the transformant was inoculated and cultured at 37° C. in ampicillin-containing 2YT medium (2L) until the absorbance of the solution at 660 nm reached 0.4. Then, IPTG (Isopropyl-β-D-thiogalactopyranoside) was added to the medium at 1 mM, and culturing continued at 30° C. for 4 hours. After the cultivation, the transformant was collected through centrifugation (6,000 rpm, 20 minutes).

EXAMPLE 8

Purification of Dna2Pho

The cultivated cells from 8 L of medium were supplemented with a double amount of 40 mM Tris-HCl buffer solution (pH 8.0), 1 tablet of protease inhibitor (Complete EDTA-free made by Roche), and 0.5 mg of Dnase RQ1 (made by Promega) to obtain a suspension. The obtained suspension was disrupted through ultrasonication. The suspension was kept at 37° C. for 10 minutes, and then centrifuged (11,000 rpm, 20 minutes) to obtain a supernatant. The supernatant was subjected to affinity chromatography on a Ni-column (Novagen, His-Bind metal chelation resin & His-Bind buffer kit). The obtained 0.5 M imidazole-eluted fraction (20 ml) was re-heated at 75° C. for 10 minutes, and centrifuged (11,000 rpm, 20 minutes) to obtain a supernatant. Then, this supernatant was adsorbed to a Hi Trap phenyl sepharose (made by Pharmacia) equilibrated with 20 mM Tris-HCl buffer solution (pH 8.0) and 2.5 M NaCl to reduce the NaCl concentration in the buffer solution from 2.5 M to 1 M so as to elute a protein of interest therefrom. The eluted protein was concentrated up to 2 ml in Centriprep YM-50 (Amicon), and then dialyzed with 20 mM Tris-HCl buffer solution (pH 8.0) and 100 mM NaCl. The resulting protein was used as a purified sample.

EXAMPLE 9

Conditions of Enzyme Reaction (1) DNA Helicase Reaction

20 µl of enzyme-reaction solution contained 50 mM HEPES buffer solution (pH 7.5), 2 mM ATP, 0.01% BSA, labeled DNA, 1 mM MbCl$_2$, 1 mM DTT, and a specific amount of enzyme. The enzyme-reaction solution was heated at 50° C. for 1 hour, and the reaction was stopped by adding EDTA thereto at a final concentration of 10 mM. The reaction product was mixed with 1/10 volume of 10× loading buffer (made by Takara), and analyzed through 15% polyacrylamide gel electrophoresis (PAGE). This electrophoresis pattern was autoradiographically visualized by PhosphoImager (made by Bio-Rad) to determine the molecular weight and the quantity of the reaction product.

Figure 1:
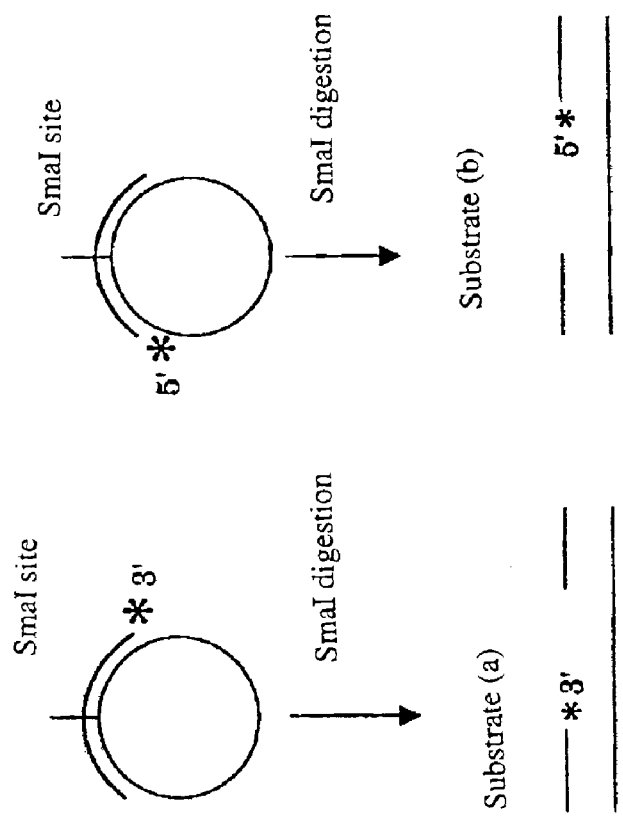
FIG. 1 is a schematic diagram showing a process of preparing two kinds of substrates to determine the unwinding direction of an enzymatic protein of the invention in a DNA helicase reaction.

(2) Determination of Unwinding Direction during DNA Helicase Reaction As shown in FIG. 1, two kinds of substrates were prepared as labeled DNA. 63 mer oligonucleotide was annealed with its complementary single-stranded M13 DNA, and the 3'-terminus of the oligonucleotide was labeled by Klenow fragment (made by Takara) and [γ-$^{32}$P] dATP. Further, another DNA was prepared by labeling the 5'-terminus of 63 mer oligonucleotide by T4 polynucleotide kinase and [γ-$^{32}$P]ATP, and then annealing it with its complementary single-stranded M13 DNA. The prepared two kinds of labeled DNA were fragmented at a SmaI site designed in the center of the complementary strand to prepare labeled substrates (a) and (b) for determining 5'-3' and 3'-5' directionalities.

Other conditions were the same as those of the above DNA helicase reaction.

(3) Measurement of Single-Stranded DNA Dependent ATPase Activity

20 µl of enzyme-reaction solution contained 50 mM HEPES buffer solution (pH 7.5), 10 µM ATP, 50 nM [γ-$^{32}$P]ATP, 0.01% BSA, dsDNA or ssDNA, 1 mM MbCl$_2$, 1 mM DTT, and a specific amount of enzyme. The enzyme-reaction solution was heated at 50° C. for 30 minutes, and the reaction was stopped by adding EDTA thereto at a final concentration of 10 mM. The reaction product was spotted on a thin-layer chromatography plate, and then developed with development liquid (1M formic acid, 0.5 M LiCl). An isolation pattern was autoradiographically visualized by PhosphoImager (made by Bio-Rad) to determine the molecular weight and the quantity of the reaction product.

(4) Measurement of Endonuclease Activity

The composition and volume of a reaction solution were the same as those in the DNA helicase reaction except that the MgCl$_2$ concentration was increased to 10 mM. 4 types (c, d, e, f) of substrates as shown in FIG. 2 were used.

The substrate c was 70 mer ssDNA having 5'-terminus labeled with T4 polynucleotide kinase and [γ-$^{32}$P]ATP.

The substrate d was RNA-DNA hybridized single-stranded molecule having the 5'-terminus of ssDNA ligated with 12 mer RNA.

The substrate e was prepared by annealing the 3'-terminus of ssDNA having labeled 5'-terminus, with its complementary ssDNA.

The substrate f was prepared by annealing the labeled 5'-terminus of ssDNA with its complementary ssDNA.

The enzyme-reaction solution was heated at 50° C. for 2 hours, and the reaction was stopped by adding 10 ml of stop liquid (90% formamide, 0.2 M EDTA (pH 8.0), 10 mg/ml BPB). The resulting solution was heated up to 100° C., and chilled on ice. Then, the solution was analyzed through 15% polyacrylamide gel electrophoresis (PAGE) containing 7 M urea. An electrophoresis pattern was autoradiographically visualized by PhosphoImager to determine the molecular weight and the quantity of the product.

EXAMPLE 10

Properties of Enzyme (1) Chemical Properties of Protein

Figure 3:
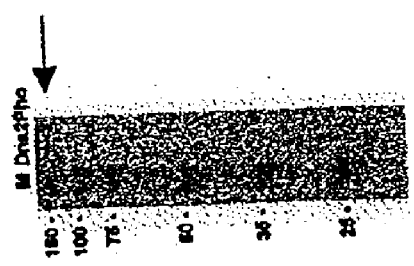
FIG. 3 is a diagram showing the results of SDS-PAGE of purified Dna2Pho.

The enzyme of interest was completely purified in the above purification process, and a single band having a molecular weight of about 150 KDa by SDS-PAGE was observed (FIG. 3). The enzyme comprises 1310 amino acid residues (SEQ ID NO:1), and a molecular weight determined from its amino-acid sequence is 151,660 Da. The enzyme had 7 conserved motifs localized on the side of C-terminus side (FIG. 4) due to its extremely low homology with the yeast protein Dna2.

(2) DNA Helicase Activity

Figure 5:
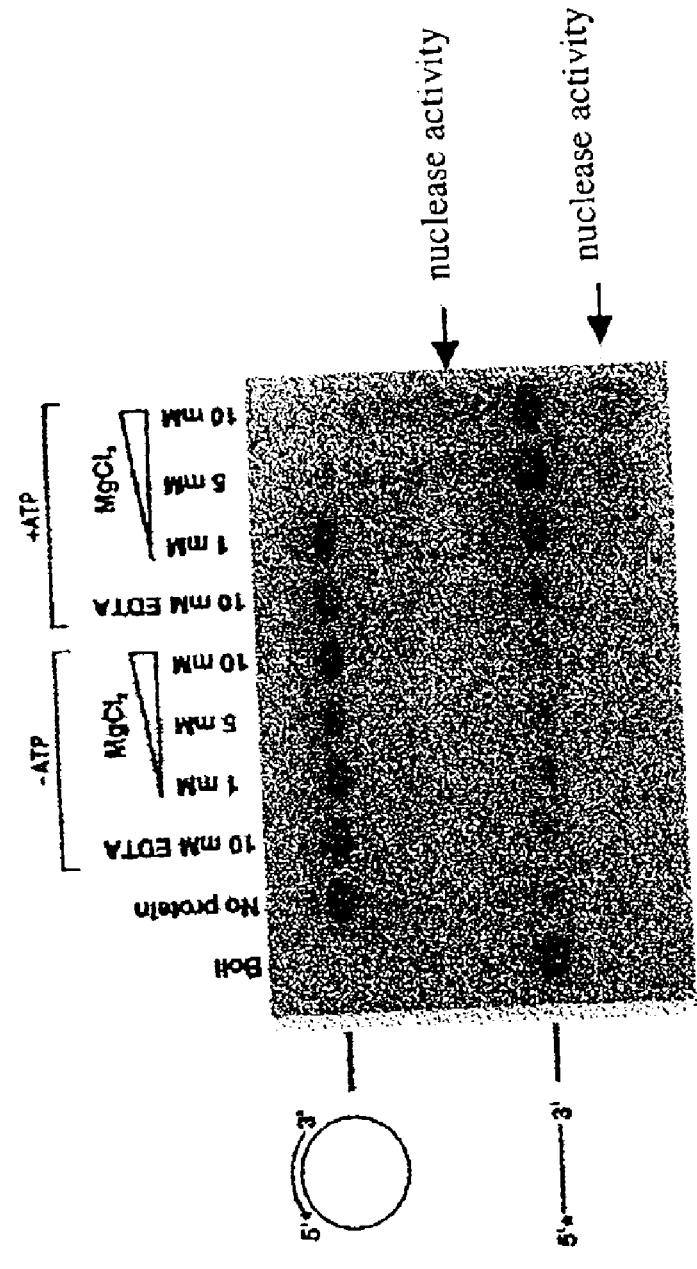
FIG. 5 is an autoradiographic picture of electrophoresis patterns of enzymatic reaction products, which shows that an enzymatic protein of the present invention has a DNA helicase activity.

The enzyme exhibited a DNA helicase activity after reaction at 50° C. for 1 hour. Coexistence of ATP and $Mg^{2+}$ ion was essential for expression of the activity. Further, when $Mg^{2+}$ ion had a concentration of 5 mM or more, both a nuclease activity and a helicase activity were observed (FIG. 5).

(3) Unwinding Direction during DNA Helicase Reaction

Figure 6:
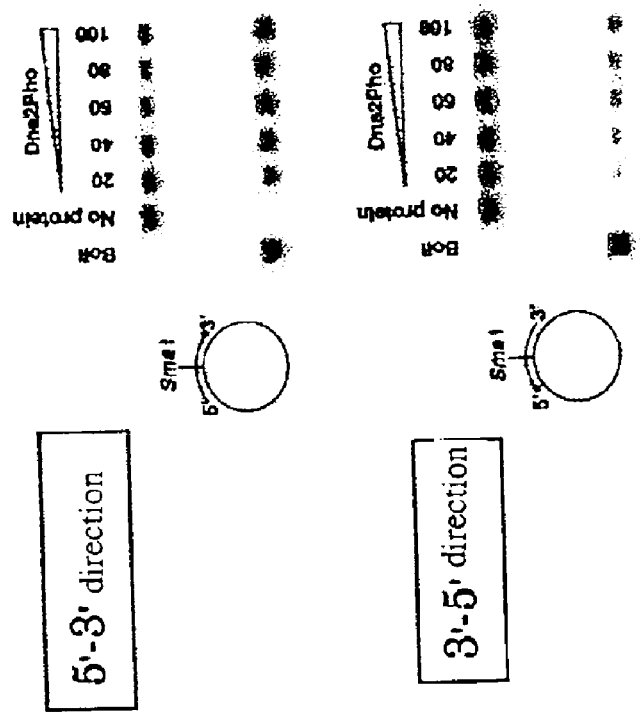
FIG. 6 is an autoradiographic picture of electrophoresis patterns of enzymatic reaction products, which shows that the enzymatic protein of the present invention unwinds doubled-stranded DNA in the 5'-3' direction during a DNA helicase reaction.

As shown in FIG. 6, Dna2Pho exhibited an unwinding activity in the 5'-3' direction.

(4) Single-Stranded DNA Dependent ATPase Activity

Figure 7:
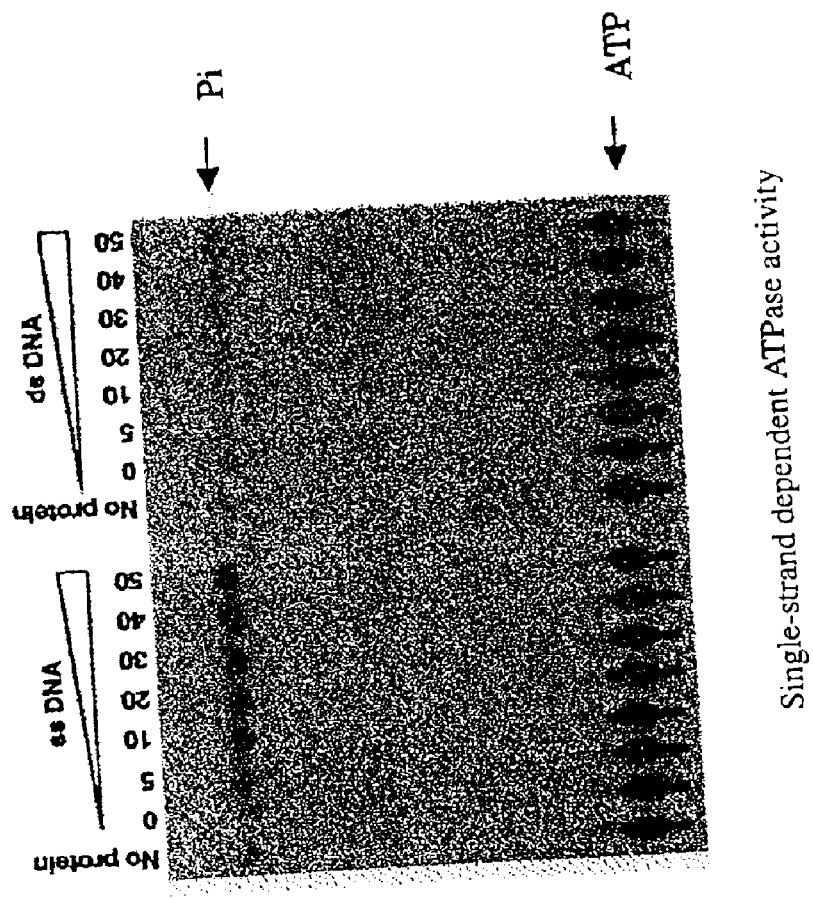
FIG. 7 is an autoradiographic picture of electrophoresis patterns of enzymatic reaction products, which shows that the enzymatic protein of the present invention has a single-strand dependent ATPase activity.

As shown in FIG. 7, Dna2Pho exhibited an ATPase activity only under coexistence with single-stranded DNA. No such effect was exhibited in Double-stranded DNA.

(5) Endonuclease Activity

As shown in FIG. 8-A, while the single-stranded DNA substrate c was decomposed to a 1 mer with time, the single-stranded substrate d containing RNA molecule at its 5'-terminus was not digested at all. In the fragmentation pattern of the single-stranded DNA substrate c, a 46 mer was developed earlier than a labeled 1 mer. This shows that fragmentation occurs in an endo-type. Further, as shown in FIG. 8-B, the substrate e having a single-stranded 5'-terminus was digested faster than the substrate f having a single-stranded 3'-terminus. The above results prove that Dna2Pho is a structure-specific endonuclease which recognizes whether the 5'-terminus of the substrate is a single strand or double strand, and DNA or RNA, and it internally causes the endo-type fragmentation in response to single-stranded DNA.

(6) Heat Stability

The enzyme exhibited excellent heat stability, a half-life period of 30 minutes or more at 75° C. in 50 mM Tris-HCl buffer solution (pH 7.5), superior to the yeast protein Dna2.

As mentioned above, the enzymatic protein according to the present invention has the structure-specific endonuclease activity in addition to the 5'-3' DNA helicase activity, and exhibits excellent heat stability. Therefore, the present invention can open the way for establishing a combinational experimental system of a DNA replication-repair conjugation system and a DNA amplification reaction (PCR) or the like to develop a new in vitro gene replication or mutation method.

What is claimed is:

1. A purified polypeptide comprising amino acids 1–1310 of SEQ ID NO:1.

2. A purified polypeptide comprising amino acids 1–1310 of SEQ ID NO:1 produced by culturing an isolated host cell transformed with an expression vector, wherein said expression vector comprises a polynucleotide molecule encoding a polypeptide comprising amino acids 1–1310 of SEQ ID NO:1, under conditions promoting expression of a polypeptide sequence comprising amino acids 1–1310 of SEQ ID NO:1.

* * * * *

SEQUENCE LISTING

<160> NUMBER OF SEQ ID NOS: 25

<210> SEQ ID NO 1
<211> LENGTH: 1310
<212> TYPE: PRT
<213> ORGANISM: Pyrococcus horikoshi

<400> SEQUENCE: 1

```
Met Glu Phe Gly Glu Leu His Pro Ser Glu Ile Ala Arg Phe Phe Glu
1               5                   10                  15

Leu Glu Glu Cys Pro Arg Phe Leu Ile Tyr Leu Asp Arg Lys Lys Lys
                20                  25                  30

Gly Glu Leu Asn Glu Tyr Ile Arg Val Ile Lys Lys Lys Glu Glu Glu
            35                  40                  45

Asn Lys Ala Leu Ala Lys Trp Gly Lys Glu Phe Glu Leu Glu Ile Leu
    50                  55                  60

Gln Gly Leu Lys Gly Arg Phe Asn Phe Pro Tyr Gly Phe Phe Lys
65                  70                  75                  80

Lys Gly Glu Glu Asp Val Thr Leu Ala Phe Phe Arg Lys Tyr Tyr Arg
                85                  90                  95

Gly Asn Val Ile Ile Phe Gly Asp Glu Glu Ala Tyr Gln Lys Phe
            100                 105                 110

Arg Glu Leu Leu Asn Leu Asn Asn Ile Leu Val Tyr Gln Ala Pro Leu
        115                 120                 125

Ile Gly Lys Ile Gly Arg Phe Lys Val Lys Gly Leu Ser Asp Phe Ile
    130                 135                 140

Ile Lys Gln Gly Asp Thr Tyr Tyr Ile Leu Glu Ala Lys Phe Thr Lys
145                 150                 155                 160

Glu Glu Lys Leu Pro His Arg Leu Gln Ala Val Ile Tyr Gly Met Leu
                165                 170                 175

Leu Asp Lys Ile Val Arg Gly Lys Ile Lys Leu Ala Ile Val Thr Lys
            180                 185                 190

Asp Asn Phe Pro Trp Pro Arg Glu Phe Leu Asp Phe Pro Asn Asp Val
        195                 200                 205
```

-continued

```
Leu Glu Phe Val Thr Thr Ile Glu Glu Lys Leu Ser Glu Glu Ile Lys
    210                 215                 220
Trp Ser Glu Ala Trp Ile Thr Ala Arg Cys Thr Thr Cys Gln Phe Glu
225                 230                 235                 240
Pro Leu Cys Leu Ser Glu Ala Leu Glu Lys Arg Ser Leu Gly Ile Leu
                245                 250                 255
Gly Ile Pro Pro Gly Asp Met Arg Val Phe Glu Lys Ile Gly Ile Arg
            260                 265                 270
Thr Ile Asp Asp Leu Ala Asn Leu Met Thr Phe Pro Thr Asp Ser Pro
        275                 280                 285
Ile Ser Phe Glu Arg Pro Gln Val Asn Asp His Asp Ala Leu Val Glu
    290                 295                 300
Ile Thr Lys Arg Thr Ser Leu Asn Val Pro Arg Leu Val Arg Ile Ala
305                 310                 315                 320
Gln Ala Val Arg Asp Glu Arg Asn Gly Lys Val Lys Arg Lys Tyr Ile
                325                 330                 335
Pro Gly Thr Gly Tyr Asn Leu Pro Tyr Asp Asp Gly Arg Leu Val Lys
            340                 345                 350
Ile Phe Ile Tyr Val Gln Asn Ser Pro Val Thr Asp Thr Leu Ile Gly
        355                 360                 365
Ile Ser Ala Leu Val Lys Ser Lys Asn Gly Glu Val Ser Val Val Glu
    370                 375                 380
Leu Val Asp Asp Val Pro Leu Asp Pro Glu Ile Gly Lys Glu Lys Glu
385                 390                 395                 400
Arg Glu Met Leu Glu Arg Phe Phe Arg Lys Val Ile Glu Val Ile Lys
                405                 410                 415
Asn Leu Ser Pro Gly Glu Glu Ile Tyr Pro His Leu Tyr Phe Tyr Thr
            420                 425                 430
Arg Gly Gln Arg Glu Ser Leu Val Asp Ala Leu Arg Arg His Arg Gly
        435                 440                 445
Leu Trp Trp Ser Lys Pro Ile Arg Ala Leu Leu Ser Leu Arg Lys Ala
    450                 455                 460
Ile Asp Trp Glu Gly Phe Ser Ile Ile Lys Asp Glu Leu Ile Glu Arg
465                 470                 475                 480
His Ala Leu Pro Phe Ala Gln Gly Leu Gly Ile Ile Pro Val Ser Ile
                485                 490                 495
Gln Phe Gly Tyr Arg Trp Lys Glu Asn Glu Ser Phe Lys Glu Ile Phe
            500                 505                 510
Glu Ile Leu Ala Arg Lys Glu Gly Glu Arg Leu Asn Leu Lys Lys Leu
        515                 520                 525
Tyr Ser Val Thr Glu His Asp Pro Ile Arg Glu Pro Tyr Tyr Pro Ala
    530                 535                 540
Leu Asn Arg Asp Asp Glu Ile Pro Phe Thr Pro Phe Trp Lys Ala
545                 550                 555                 560
Leu Val Glu Gly Ile Thr Lys Asp Pro Arg Lys Ile Asn Asp Val Lys
                565                 570                 575
Asp Met Leu Glu Gln Val Val Arg Ala Met Ala Lys Ile Glu Glu Glu
            580                 585                 590
Ile Pro Glu Arg Tyr Lys Glu Phe Thr Lys Lys Glu Gly Ile Pro Lys
        595                 600                 605
Lys Glu Phe Glu Ser Phe Asp Leu Glu Asp Gly Asp Leu Ala Arg Val
    610                 615                 620
```

-continued

```
Leu Ile Glu Tyr Leu Leu Glu Phe His Ser Arg Lys Gly Gln Leu
625                 630                 635                 640

Glu Arg Tyr Tyr Arg Ile Pro Glu Glu Ile Arg Ala Tyr Ser Glu Lys
                645                 650                 655

Ser Ala Ile Val Arg Ile Glu Ser Ile Glu Arg Lys Thr Asn Gly Glu
                660                 665                 670

Cys Val Ile Lys Gly Lys Ile Val Leu Pro Ser Asp Gly Phe Lys
                675                 680                 685

Gly Tyr Ser Pro Glu Glu Val Leu Val Asp Ile Asp Glu Asp Ser Trp
            690                 695                 700

Val Tyr Val Thr Pro Leu Ser Ile Leu Gly Gly Asp Asp Pro Ala Lys
705                 710                 715                 720

Ile Ile Lys Arg Ser Pro Leu Gly Val Ile Glu Tyr Ile Asn His Arg
                725                 730                 735

Asp Gly Arg Ile Ile Leu Lys Leu Thr Asn Val Pro Pro Gly Lys Phe
                740                 745                 750

Thr Leu Arg His Ser Lys Ser Lys Cys Arg Asn Gly Val Ile Asn Ile
            755                 760                 765

Glu Gly Val Lys Ile His Leu Gly Asp Tyr Ile Ile Leu Asp Pro Ala
770                 775                 780

Ile Asp Glu Ile Gly Met Ser Arg Ala Phe Glu Val Leu Asp Lys Ile
785                 790                 795                 800

Asn Glu Glu Ala His Glu Val Tyr Arg Leu Leu Asn Glu Ile Tyr Glu
                805                 810                 815

Gly Asn Thr Asn Ile Asn Pro Glu Ile Gly Val Trp Lys Lys Glu Tyr
                820                 825                 830

Ile Gln Glu Phe Leu Asn Phe Leu Pro Ser Leu Asn Arg Glu Gln Val
            835                 840                 845

Asn Phe Ala Leu Asp Cys Glu His Arg Ile Val Thr Leu Gln Gly Pro
850                 855                 860

Pro Gly Thr Gly Lys Thr Ser Gly Ala Ile Ala Pro Ala Ile Leu Ala
865                 870                 875                 880

Arg Ala Tyr Ser Thr Ile Lys Gln Gly Lys Ser Ser Leu Phe Ile Val
                885                 890                 895

Thr Ala Leu Ser His Arg Ala Val Asn Glu Ala Leu Ile Arg Thr Tyr
                900                 905                 910

Lys Leu Lys Glu Lys Leu Lys Asp Ile Lys Glu Leu Lys Asn Val Glu
            915                 920                 925

Leu Ile Arg Gly Val Ser Ser Glu Glu Ala Val Lys Pro Met Glu Lys
            930                 935                 940

Glu Leu Asn Gly Leu Lys Val Asn Val Thr Asn Lys Phe Ser Phe Ser
945                 950                 955                 960

Lys Ser Pro Leu Phe Leu Thr Val Lys Ile Leu Phe Ala Thr Pro Gln
                965                 970                 975

Thr Ala Phe Lys Leu Ala Lys Asp Tyr Asp Ala Asp Leu Val Val Ile
                980                 985                 990

Asp Glu Ala Ser Met Leu Asp Leu Pro Met Phe Phe Leu Ala Thr Ser
            995                 1000                1005

Asn Ala Lys Gly Gln Val Leu Leu Val Gly Asp His Arg Gln Met
            1010                1015                1020

Gln Pro Ile Gln Val His Glu Trp Glu Leu Glu Asp Arg Lys Thr
            1025                1030                1035
```

```
Ile Glu Glu His Leu Pro Phe Leu Ser Val Leu Asn Phe Ile Arg
    1040            1045                1050

Phe Leu Arg Gly Glu Leu Glu Arg Glu Leu Lys Arg Phe Lys
    1055            1060                1065

Arg Ile Leu Gly Arg Asp Pro Pro Arg Trp Asn Val Asp Lys Asp
    1070            1075                1080

Arg Val Leu Pro Met His Arg Leu Arg Glu Thr Phe Arg Leu Pro
    1085            1090                1095

Arg Ala Leu Ala Lys Leu His Ser Glu Leu Phe Tyr Ser Phe Asp
    1100            1105                1110

Gly Ile Glu Leu Ile Ser Arg Lys Asn Ser Asp Arg Glu Val Leu
    1115            1120                1125

Glu Thr Leu Lys Lys Ala Gly Lys Asp Glu Phe Leu Lys Phe Ile
    1130            1135                1140

Leu Asp Pro Gly Tyr Pro Val Ile Leu Ile Ile His Asn Glu Gly
    1145            1150                1155

Gly Ser Thr Lys Val Asn Glu Leu Glu Ala Glu Ile Val Lys Asp
    1160            1165                1170

Ile Leu Lys Glu Val Lys Gly Ile Asp Val Gly Val Val Pro
    1175            1180                1185

Tyr Arg Ala Gln Lys Arg Leu Ile Arg Ser Leu Val Asn Val Gln
    1190            1195                1200

Val Asp Thr Val Glu Arg Phe Gln Gly Gly Glu Lys Asp Val Ile
    1205            1210                1215

Ile Val Ser Met Thr Ser Ser Asp Pro Ala Tyr Leu Ser Lys Val
    1220            1225                1230

Leu Glu Phe Ile Tyr Asn Pro Asn Arg Leu Asn Val Ala Gly Ser
    1235            1240                1245

Arg Ala Lys Glu Lys Leu Ile Leu Ile Ala Ser Lys Asn Leu Phe
    1250            1255                1260

Thr Leu Ser Ala Lys Asp Leu Glu Thr Phe Glu Ile Leu Arg Pro
    1265            1270                1275

Trp Lys Arg Phe Tyr Ile Lys Met Arg Arg Glu Gly Glu Ser Arg
    1280            1285                1290

Lys Phe Thr Lys Ala Asp Tyr Ile Leu Glu Val Phe Arg Trp Ala
    1295            1300                1305

Gly Glu
    1310

<210> SEQ ID NO 2
<211> LENGTH: 3933
<212> TYPE: DNA
<213> ORGANISM: Pyrococcus horikoshi

<400> SEQUENCE: 2
ttggaatttg gggagttaca tcccagcgaa atcgcaaggt tctttgaact agaggagtgt      60
ccaagatttt taatttacct tgataggaag aagaaaggag agctgaacga atacattagg     120
gtcattaaaa agaaagagga agaaaataag gcattagcaa agtggggaaa ggaatttgaa     180
cttgaaatcc tccagggct taaagtagg tttaactttc ccttctatgg attttttaag      240
aagggagaag aggatgtaac gcttgcattt tttaggaagt actatagagg gaacgttata     300
atattcgggg acgaagagga ggcttaccaa aagttcagag agcttttaaa cctgaacaat     360
atcctcgtgt atcaagctcc actcatagga aagatagggga ggtttaaagt taaagggctc     420
```

-continued

```
tcggatttca taataaagca gggagatacc tactacattc ttgaggctaa gtttacaaag      480
gaagagaagc tacctcacag gcttcaggcc gttatatacg gaatgctact cgataagata      540
gtcagaggta aaataaagct agccattgtc actaaggata attttccctg gccccgggag      600
tttttagatt tcccgaacga cgttttagag tttgtaacaa cgatagaaga aaagctgagt      660
gaagagatca aatggagcga agcctggata acggcaagat gtacaacgtg ccaattcgag      720
cctttgtgcc tctcggaagc ccttgagaag aggagcctcg gaatcctggg gataccctccg     780 ggggatatga gggtattcga aaaatagga ataaggacga tagatgacct cgcaaaccta       840
atgacatttc caactgacag ccccataagc tttgagagac cccaggtaaa tgaccatgat      900
gccttagttg agataaccaa agaacgagc ctaaatgtac caaggctcgt aaggattgcc       960
caagcagtta gggatgaaag gaatggtaaa gttaaaagga agtacatccc aggaacagga     1020
tataaccttc cctatgatga tggacggtta gttaaaatct ttatatacgt tcaaaacagc     1080
ccagtaaccg atacgctcat cggaatctcg gccttagtta aatcaaagaa cggagaagtg     1140
tccgttgttg aactagttga tgacgttccc ctagatccag agatagggaa ggaaaaggag     1200
agggagatgc ttgagaggtt cttcaggaaa gtaatagaag ttataaagaa cctctcacct     1260
ggtgaggaaa tttaccccca tctatacttt tacacaaggg gacagaggga gagcctcgta     1320
gatgccctta gaaggcacag gggactgtgg tggagcaaac caattagggc ccttttaagc     1380
ttaaggaagg ccatagactg gaagggttc tcgataatta aggatgaact aatagagagg      1440
catgcattac ccttcgccca gggattggga ataataccag tttcaatcca gttcgggtac     1500
aggtggaaag aaaacgaatc tttcaaggag atctttgaaa tcctggcaag gaaggaaggt     1560
gaaaggctca acttgaaaaa gctctacagc gtaacagagc acgatccaat aagggagcca     1620
tactatccgg ccttgaatag agatgacgac gagatcccat tcaccccatt ctggaaagct     1680
ctagttgagg ggataactaa ggatcccaga agatagaaacg acgttaagga tatgctagag     1740
caagtagtga gagctatggc aaagatagag gaagaaattc agaaagata taaagagttc       1800 acgaaaaagg aggggatacc taaaaaggag tttgaaagct tcgatcttga agatggggat      1860
ttggccaggg ttctgatcga gtacttactc ctggaatttc actctagaaa gggccaactc     1920
gagaggtatt accggatccc tgaagagata agggcctatt ctgaaaaatc tgcaattgtt     1980
aggattgaga gtatagagag gaaaacaaat ggagaatgtg taataaaggg gaaaatagtc     2040
cttccgagtg atgacggttt taaggggtac tcacccgagg aggttctagt agatattgac     2100
gaggattcct gggtgtacgt aactcctctt agtatttag gaggggatga tccagctaaa      2160
ataataaaga ggtctccact tggggtcatc gagtatataa accatagaga tggaaggata     2220
atcctaaagc taaccaacgt accccccagga aagttcaccc ttcggcactc aaaaagtaaa     2280
tgcaggaatg gagtgattaa catcgagggg gtaaagatcc acctaggaga ttacataatc     2340
ctagatccag ccatcgatga aataggaatg tcaagggcat ttgaggttct cgacaagatt     2400
aatgaagaag cccacgaggt atataggctt taaatgaga tatatgaggg aaatacgaat       2460
attaatcccg aaattggggt ttggaaaaaa gaatatattc aggaattcct aaactttctt     2520
cccagcctaa atagggaaca ggttaacttt gcactagact gcgagcatag aatagtaacc     2580
cttcaagggc ctccaggaac cgggaagacc tcaggagcaa tagctccagc aattcttgca     2640
agggcatatt caacgataaa gcaaggaaaa agctccctat ttatagtgac ggccctctcc     2700 cataggccg ttaacgaagc tctaataagg acgtataagc ttaaagagaa gttgaaagat     2760
```

```
atcaaagaac tcaagaatgt agagcttata aggggagtct caagcgaaga agctgtaaaa    2820
cccatggaaa aggagttaaa tggactgaaa gttaatgtga caaataaatt ttcattttca    2880
aagtctcctc tctttctaac ggtaaagatt ctctttgcaa cacctcaaac agcgtttaaa    2940
cttgcaaaag attatgatgc agacctcgtg gtgatagatg aagcaagcat gctggactta    3000
ccaatgttct tcttggcaac gagtaatgca aagggccagg tgttgctagt agggatcat     3060 agacagatgc aaccgattca agttcatgag tgggagctag aagataggaa aaccattgaa    3120
gagcacttac ccttcctttc ggttttaaac ttcataaggt tcctgagagg agagctcgag    3180
gaaagggagc ttaagagggtt taagagaatt ctgggtagaa atccaccaag gtggaatgtc    3240
gataaagatc gcgtcctccc aatgcacagg cttagagaaa ctttcagact cccaagagca    3300
ttagccaagt tacattcaga gctcttctac tccttcgatg ggatagaatt aataagcagg    3360
aaaaactcag atagagaagt cctggaaacg ctgaaaaaag cagggaaaga cgagttccta    3420
aagttcattc tagatccagg gtatccagta attttgataa tccataacga gggggctca    3480 accaaggtta acgagttaga agctgagata gtaaaggata ttctaaagga ggttaaaggc    3540
atcgatgtag gtgtcgttgt tccttacagg gcccagaaga ggctaataag aagccttgta    3600
aacgttcagg ttgataccgt tgagagattc caggggggag aaaaggatgt cataatagtt    3660
tccatgacat ccagcgatcc agcttacctc tcaaaggttc tggaattcat atataatccc    3720
aatagactga acgtcgccgg tagtagggcc aaggaaaagc taatactaat agcatcaaag    3780
aatttgttca cgctttctgc gaaggatttg gaaaccttcg agatactaag gccatggaag    3840
aggttctata taaaaatgag aagggaagga gaaagtagga aatttacaaa agctgattac    3900
atattagaag tgtttaggtg ggctggagag taa                                 3933

<210> SEQ ID NO 3
<211> LENGTH: 44
<212> TYPE: DNA
<213> ORGANISM: Artificial Sequence
<220> FEATURE:
<223> OTHER INFORMATION: PCR primer

<400> SEQUENCE: 3
gtagaggtgg aaacatatgg aatttgggga gttacatccc agcg                     44

<210> SEQ ID NO 4
<211> LENGTH: 48
<212> TYPE: DNA
<213> ORGANISM: Artificial Sequence
<220> FEATURE:
<223> OTHER INFORMATION: PCR primer

<400> SEQUENCE: 4
ctcgagtgcg gccgcaagct tgtcgacctc tccagcccac ctaaacac                 48

<210> SEQ ID NO 5
<211> LENGTH: 14
<212> TYPE: PRT
<213> ORGANISM: S. cerevisiae

<400> SEQUENCE: 5

Ile Leu Gly Met Pro Gly Thr Gly Lys Thr Thr Val Ile Ala
1               5                   10

<210> SEQ ID NO 6
<211> LENGTH: 17
<212> TYPE: PRT
```

<213> ORGANISM: S. cerevisiae

<400> SEQUENCE: 6

Leu Leu Thr Ser Tyr Thr His Ser Ala Val Asp Asn Ile Leu Ile Lys
1               5                   10                  15
Leu

<210> SEQ ID NO 7
<211> LENGTH: 11
<212> TYPE: PRT
<213> ORGANISM: S. cerevisiae

<400> SEQUENCE: 7

Tyr Val Ile Leu Asp Glu Ala Ser Gln Ile Ser
1               5                   10

<210> SEQ ID NO 8
<211> LENGTH: 12
<212> TYPE: PRT
<213> ORGANISM: S. cerevisiae

<400> SEQUENCE: 8

Phe Ile Met Val Gly Asp His Tyr Gln Leu Pro Pro
1               5                   10

<210> SEQ ID NO 9
<211> LENGTH: 16
<212> TYPE: PRT
<213> ORGANISM: S. cerevisiae

<400> SEQUENCE: 9

Glu Ser Val Ala Glu Leu Thr Leu Gln Tyr Arg Met Cys Gly Asp Ile
1               5                   10                  15

<210> SEQ ID NO 10
<211> LENGTH: 19
<212> TYPE: PRT
<213> ORGANISM: S. cerevisiae

<400> SEQUENCE: 10

Ile Leu Thr Ala Asp Gln Phe Gln Gly Arg Asp Lys Lys Cys Ile Ile
1               5                   10                  15
Ile Ser Met

<210> SEQ ID NO 11
<211> LENGTH: 11
<212> TYPE: PRT
<213> ORGANISM: S. cerevisiae

<400> SEQUENCE: 11

Arg Val Asn Val Ala Met Thr Arg Ala Lys Ser
1               5                   10

<210> SEQ ID NO 12
<211> LENGTH: 14
<212> TYPE: PRT
<213> ORGANISM: S. pombe

<400> SEQUENCE: 12

Ile Leu Gly Met Pro Gly Thr Gly Lys Thr Thr Thr Ile Ser
1               5                   10

<210> SEQ ID NO 13

```
<211> LENGTH: 17
<212> TYPE: PRT
<213> ORGANISM: S. pombe

<400> SEQUENCE: 13

Leu Leu Thr Ser Phe Thr His Leu Ala Val Asp Asn Ile Leu Ile Lys
1               5                   10                  15
Ile

<210> SEQ ID NO 14
<211> LENGTH: 11
<212> TYPE: PRT
<213> ORGANISM: S. pombe

<400> SEQUENCE: 14

Tyr Cys Ile Ile Asp Glu Ala Ser Gln Ile Pro
1               5                   10

<210> SEQ ID NO 15
<211> LENGTH: 12
<212> TYPE: PRT
<213> ORGANISM: S. pombe

<400> SEQUENCE: 15

Phe Val Leu Val Gly Asp His Tyr Gln Leu Pro Pro
1               5                   10

<210> SEQ ID NO 16
<211> LENGTH: 16
<212> TYPE: PRT
<213> ORGANISM: S. pombe

<400> SEQUENCE: 16

Glu Ala Val Thr Thr Leu Arg Leu Gln Tyr Arg Met Asn Glu Asp Ile
1               5                   10                  15

<210> SEQ ID NO 17
<211> LENGTH: 19
<212> TYPE: PRT
<213> ORGANISM: S. pombe

<400> SEQUENCE: 17

Ile Asn Thr Val Asp Arg Tyr Gln Gly Arg Asp Lys Asp Ile Ile Leu
1               5                   10                  15
Ile Ser Phe

<210> SEQ ID NO 18
<211> LENGTH: 11
<212> TYPE: PRT
<213> ORGANISM: S. pombe

<400> SEQUENCE: 18

Arg Leu Asn Val Ala Leu Ser Arg Ala Lys Val
1               5                   10

<210> SEQ ID NO 19
<211> LENGTH: 14
<212> TYPE: PRT
<213> ORGANISM: P. horikoshii

<400> SEQUENCE: 19

Leu Gln Gly Pro Pro Gly Thr Gly Lys Thr Ser Gly Ala Ile
1               5                   10
```

-continued

```
<210> SEQ ID NO 20
<211> LENGTH: 17
<212> TYPE: PRT
<213> ORGANISM: P. horikoshii

<400> SEQUENCE: 20

Ile Val Thr Ala Leu Ser His Arg Ala Val Asn Glu Ala Leu Ile Arg
1               5                   10                  15
Thr

<210> SEQ ID NO 21
<211> LENGTH: 11
<212> TYPE: PRT
<213> ORGANISM: P. horikoshii

<400> SEQUENCE: 21

Leu Val Val Ile Asp Glu Ala Ser Met Leu Asp
1               5                   10

<210> SEQ ID NO 22
<211> LENGTH: 12
<212> TYPE: PRT
<213> ORGANISM: P. horikoshii

<400> SEQUENCE: 22

Val Leu Leu Val Gly Asp His Arg Gln Met Gln Pro
1               5                   10

<210> SEQ ID NO 23
<211> LENGTH: 16
<212> TYPE: PRT
<213> ORGANISM: P. horikoshii

<400> SEQUENCE: 23

Gly Ile Asp Val Gly Val Val Pro Tyr Arg Ala Gln Lys Arg Leu
1               5                   10                  15

<210> SEQ ID NO 24
<211> LENGTH: 19
<212> TYPE: PRT
<213> ORGANISM: P. horikoshii

<400> SEQUENCE: 24

Val Asp Thr Val Glu Arg Phe Gln Gly Gly Glu Lys Asp Val Ile Ile
1               5                   10                  15
Val Ser Met

<210> SEQ ID NO 25
<211> LENGTH: 10
<212> TYPE: PRT
<213> ORGANISM: P. horikoshii

<400> SEQUENCE: 25

Arg Leu Asn Val Ala Gly Ser Arg Ala Lys
1               5                   10
```